United States Patent
Barthelmes et al.

(10) Patent No.: US 11,426,743 B2
(45) Date of Patent: Aug. 30, 2022

(54) LIQUID TANK FOR AN ATOMIZER

(71) Applicant: J. Wagner GmbH, Markdorf (DE)

(72) Inventors: Jan Barthelmes, Salem (DE); Thomas Jeltsch, Friedrichshafen (DE); Holger Stohl, Markdorf (DE)

(73) Assignee: J. Wagner GmbH, Markdorf (DE)

( * ) Notice: Subject to any disclaimer, the term of this patent is extended or adjusted under 35 U.S.C. 154(b) by 79 days.

(21) Appl. No.: 16/658,613

(22) Filed: Oct. 21, 2019

(65) Prior Publication Data

US 2020/0114378 A1 Apr. 16, 2020

Related U.S. Application Data

(63) Continuation of application No. PCT/EP2018/060122, filed on Apr. 19, 2018.

(30) Foreign Application Priority Data

Apr. 21, 2017 (DE) ..................... 10 2017 108 615.3

(51) Int. Cl.
| | |
|---|---|
| *B05B 5/16* | (2006.01) |
| *B05B 5/08* | (2006.01) |
| *B05B 11/00* | (2006.01) |
| *B65D 83/00* | (2006.01) |
| *B65D 21/02* | (2006.01) |

(Continued)

(52) U.S. Cl.
CPC ............ *B05B 5/1666* (2013.01); *B05B 5/087* (2013.01); *B05B 5/1675* (2013.01); *B05B 11/0037* (2013.01); *B65D 21/0204* (2013.01); *B65D 83/0055* (2013.01); *A45D 34/00* (2013.01); *A61M 35/00* (2013.01); *B05B 5/1691* (2013.01)

(58) Field of Classification Search
CPC ... B05B 5/1666; B05B 11/0037; B05B 5/087; B05B 5/1675; B05B 5/1691; B65D 21/0204; B65D 83/0055; A61M 35/00; A45D 34/00; A45D 2200/052
See application file for complete search history.

(56) References Cited

U.S. PATENT DOCUMENTS 3,281,006 A * 10/1966 Wei .................. A47J 27/13
220/4.27
4,275,846 A * 6/1981 Coffee ............... B05B 5/16
239/690

(Continued)

FOREIGN PATENT DOCUMENTS

| CN | 85105717 A | 1/1987 |
|---|---|---|
| CN | 1291957 A | 4/2001 |

(Continued)

OTHER PUBLICATIONS

Chinese Office Action (Application No. 201880040131.9) dated Nov. 12, 2020 (English translation only).

(Continued)

*Primary Examiner* — Donnell A Long
(74) *Attorney, Agent, or Firm* — Burr & Brown, PLLC

(57) ABSTRACT

A liquid tank for an electrostatic atomizer for liquids is provided, including a receiving space for a liquid and a delimiting wall delimiting the receiving space with respect to the surrounding area. The liquid tank further includes a self-closing valve connecting the liquid tank to the atomizer.

11 Claims, 4 Drawing Sheets

(51) Int. Cl.
   *A45D 34/00* (2006.01)
   *A61M 35/00* (2006.01)

(56) References Cited

U.S. PATENT DOCUMENTS

| | | | | |
|---|---|---|---|---|
| 4,356,528 | A | * | 10/1982 | Coffee ................ B05B 5/04 |
| | | | | 118/626 |
| 4,612,598 | A | | 9/1986 | Norris |
| 4,925,066 | A | * | 5/1990 | Rosenbaum ........ B05B 11/0037 |
| | | | | 222/129 |
| 5,221,050 | A | | 6/1993 | Jeffries et al. |
| 6,267,274 | B1 | | 7/2001 | Smrt |
| 6,685,691 | B1 | | 2/2004 | Freund et al. |
| 8,844,584 | B1 | * | 9/2014 | Haley ................... B65B 3/17 |
| | | | | 141/20 |
| 2003/0205580 | A1 | | 11/2003 | Yahav |
| 2007/0152086 | A1 | | 7/2007 | Yamaguchi et al. |
| 2009/0057347 | A1 | * | 3/2009 | Leys ................ B67D 1/0462 |
| | | | | 222/386.5 |
| 2009/0200392 | A1 | | 8/2009 | Duru et al. |
| 2009/0261127 | A1 | * | 10/2009 | Pan ................. B05B 11/0038 |
| | | | | 222/256 |
| 2012/0267388 | A1 | * | 10/2012 | Tom .................. B65D 83/0055 |
| | | | | 222/1 |
| 2013/0037575 | A1 | | 2/2013 | van der Molen |
| 2013/0284766 | A1 | * | 10/2013 | Dubois ................ B05B 9/0861 |
| | | | | 222/386.5 |
| 2014/0202975 | A1 | * | 7/2014 | Tom .................... B67D 7/025 |
| | | | | 215/12.1 |
| 2015/0190822 | A1 | | 7/2015 | Kobayashi et al. |
| 2017/0079328 | A1 | | 3/2017 | Wu |
| 2017/0270774 | A1 | * | 9/2017 | Fateh ................ B65D 51/245 |
| 2019/0218001 | A1 | * | 7/2019 | Vredevoogd ...... B65D 47/0804 |

FOREIGN PATENT DOCUMENTS

| | | |
|---|---|---|
| CN | 201308841 Y | 9/2009 |
| CN | 204703879 U | 10/2015 |
| CN | 105057157 A | 11/2015 |
| CN | 106069844 A | 11/2016 |
| GB | 2 061 769 A | 5/1981 |
| JP | S64-027658 A | 1/1989 |
| JP | 2007-521950 A | 8/2007 |
| JP | 2008-212857 A1 | 9/2008 |
| JP | 2013-522133 A | 6/2013 |
| KR | 10-0229943 B1 | 11/1999 |
| KR | 10-2012-0072374 A | 7/2012 |
| WO | 2005/072059 A2 | 8/2005 |
| WO | 2011/037112 A1 | 3/2011 |
| WO | 2014/103116 A1 | 7/2014 |

OTHER PUBLICATIONS

English translation of International Preliminary Report on Patentability (Chapter I) (Application No. PCT/EP2018/060122) dated Oct. 31, 2019, 10 pages.
International Search Report and Written Opinion (Application No. PCT/EP2018/060122) dated Jun. 13, 2018.
Chinese Office Action (Application No. 201880040131.9) dated Nov. 2, 2021 (with English translation).
Japanese Office Action (Application No. 2019-557465) dated Jan. 5, 2022 (with English translation).
European Office Action (Application No. 18 719 154.9) dated Nov. 5, 2020.
Korean Office Action (with English translation) dated Jun. 21, 2022 (Application No. 10-2019-7034214).

* cited by examiner

LIQUID TANK FOR AN ATOMIZER

CROSS REFERENCE TO RELATED APPLICATIONS

This application is a continuation of International Application No. PCT/EP2018/060122 filed Apr. 19, 2018, which designated the United States, and claims the benefit under 35 USC § 119(a)-(d) of German Application No. 10 2017 108 615.3 filed Apr. 21, 2017, the entireties of which are incorporated herein by reference.

FIELD OF THE INVENTION

The present invention relates to a liquid tank for an atomizer.

BACKGROUND OF THE INVENTION

Atomizers, in particular, in the area of household items and cosmetics, are generally hand-operated or are actuated by pressure differences applied in a motorized manner.

The media to be atomized, generally liquids, are in this case provided in liquid tanks on the atomizer. After emptying a liquid tank, it is exchanged and replaced by a tank with a fresh filling. The liquid tank is then disposed of or sent to a recycling system.

It is disadvantageous that corresponding systems do not allow an exchange of different liquids to be available at the atomizer.

SUMMARY OF THE INVENTION

The present invention provides a liquid tank for an atomizer for liquids, in particular, an electrostatic atomizer, the liquid tank comprising a receiving space for a liquid and a delimiting wall for delimiting the receiving space with respect to the surrounding area. The present invention is characterized in that the liquid tank comprises a self-closing valve for connection to the atomizer.

In the context of the present invention, electrostatic atomization comprises all atomization processes that atomize liquids with effects under the influence of a high voltage. In particular, electrohydrodynamic effects and electrokinetic effects are also covered by the concept of this type of atomization. In the context of the present invention, electrostatic atomization may also be understood as meaning electrohydrodynamic atomization.

The use of a self-closing valve allows the liquid tank to be removed from the atomizer even without complete emptying and another liquid tank to be connected and makes it possible for the liquids to be exchanged according to the particular use. This is appropriate, in particular, for so-called electrostatic atomizers, which are the subject of inventions of the applicant. In particular, in the case of electrostatic atomizers that are suitable for the application of different liquids such as not only paints or lacquers but also, for example, in special forms of construction, for cosmetics, a flexible exchangeability of, for example, different cosmetic properties or specifications for use is indispensable.

The liquid tank is connected by way of the valve to an atomizer and brought into contact with the line system of the latter, and when the valve is in contact a dispensing of liquid is made possible by opening the valve. As soon as the liquid tank is removed from the atomizer, the valve closes of its own accord. An additional covering, for example, a screw closure, is not required, but may be additionally provided.

In a preferred embodiment, the self-closing valve is formed as a diaphragm valve, as a lip valve, as a ball valve or a spring valve.

Such valves usually have an inactive position, in which they are closed if they are not subjected to the action of an external mechanical mechanism, in particular, an opening mechanism. In an individual case, for example, in the case of a ball valve or a lip valve, the sealing effect may also be brought about by pressure being applied from the interior of the receiving space, so that, to release the liquid when a connection to an atomizer is made, the ball has to be moved against this pressure, counter to the normal direction of flow of the liquid to be removed. Pressure may similarly be applied to diaphragm valves or spring valves.

A lip valve allows a flow in a direction through valve lips arranged in line in the normal direction of flow. When there is a flow counter to the normal direction of flow, these valve lips are pressed against one another and the cross section is constricted until there is a sealing closure. Combinations of such valves also allow different flow paths with different flow directions, for example, branching off when there is a backflow into a disposal space for excess material that should not get back into the liquid tank.

In a further embodiment of the present invention, it is provided that the delimiting wall and/or a housing surrounding the delimiting wall consists of insulating material, in particular, forms an electrostatic shielding, the material preferably having a dielectric strength of at least 30 kV and/or having, in particular, a wall thickness of at least 1 mm.

Generally used in the case of electrostatic atomizers is a high voltage, which can inter alia also charge the stored liquid. Because the liquid is generally at least slightly conductive, the high voltage required for the atomization is also present at the liquid in the liquid tank. Consequently, an insulation with respect to the outside is required, in order to avoid an electric shock or an electrostatic discharge to the user. Particularly, preferably, polypropylene, ABS, PTFE, polyethylenes or polyesters may be used here as the material for the housing.

Preferably, the housing may also contain an aeration opening, in order, for example, to aerate the interior space with respect to the outside.

In a development, it may be provided that the delimiting wall and/or a housing surrounding the delimiting wall comprises a contacting to a reference potential with respect to a high voltage, for example, a common negative pole of a high-voltage source and a storage battery, the contacting having at least one contact for connecting to the electrostatic atomizer. The housing may for this purpose comprise, in particular, a conductive outer layer, which is attached to the contacting.

By the contacting, it can additionally or alternatively be ensured that the electrostatic discharge to the user described above is avoided.

In one particular embodiment of the present invention, at least one detector for identifying (coding) the liquid tank is comprised on the liquid tank, the detector being formed, in particular, as mechanical coding, preferably for forming an interlocking engagement, and/or electronic coding, in particular, for transmitting information about the liquid tank, and/or electrical coding, in particular, for forming electrical line routes via contacts.

The detector for identification may be formed, in particular, as an RFID marking or the like, the RFID marking being able to be both read and fully or partially written by the atomizer, in particular, its control electronics. Writing is advantageous, in particular, whenever data on use, such as, for example, the date of the first opening of the liquid tank, or data concerning the amount of liquid removed are to be stored. As a result, the exchangeability of the liquid tank is optimized.

The detector allows a device parameter to be preselected on an atomizer. Moreover, liquid tanks that are possibly not intended to be used can be identified and their use avoided. Also, the possibly required cleaning of an atomizer can be signaled to the user by an identification of the liquid tank, in order to obtain a desired result. After cosmetics are used, for example, the device should be cleaned before a liquid tank with deodorant is used. The device can draw attention to this when there is identification of the liquid tanks.

The mechanical coding may, for example, be realized by holes, projections or notches. An electronic coding, for example, by way of resistors, an identification chip or an RFID, may contain additional information, which, for example, provides a use-by date or the like. A purely electrical coding may be performed, for example, by the provision of line routes or electrical bridges.

In a particularly preferred embodiment, it is provided that the delimiting wall is formed as flexible, in particular, as a collapsible bag, or that the delimiting wall is formed as a cylinder, preferably with a passively guided follow-up piston or piston head.

A self-collapsing design of the delimiting wall offers the advantage that emptying is made possible without additional mechanical aeration of a receiving space. The possibility of a passive follow-up piston also allows emptying without bringing about any additional mechanical effects or opening of the receiving space. The liquid stored is in this way always sealed with respect to the surrounding area, and can consequently satisfy the corresponding requirements, for example, in terms of hygiene.

Preferably, at least one further receiving space for at least one further liquid may be comprised on the liquid tank according to the present invention. In this case, a further delimiting wall for delimiting the receiving space with respect to the surrounding area and the first receiving space is similarly provided.

A further receiving space makes it possible to provide a number of components in a liquid tank. Thus, for example, a paint may be adapted, by setting a mixing ratio of two shades of color, or possibly a cosmetic material may be adapted, by mixing a carrier fluid and a cosmetic component, to suit a desired effect in terms of appearance or action. Other variants involving a number of components are also conceivable.

In a preferred embodiment, it is provided that at least one filling level indicator for indicating the filling level of the liquid in the receiving space is comprised.

The filling level indicator may be realized mechanically, for example, by a viewing window, or electronically, for example, by a volume flow sensor. Other types of detection of the amount of liquid removed are also conceivable, for example, by logging pump parameters such as running time or revolutions of the pump motor when the pump geometry is known.

What is more, it is also provided that at least one sensor element for detecting the ambient parameters of the liquid tank and/or the liquid is comprised, the sensor element having, in particular, a memory element for storing the ambient parameters.

A sensor, for example, a temperature sensor or the like, allows an effect of the ambient parameters on the liquid to be detected. If it is, for example, stored while too hot or too cold, the liquid may denature, which is indicated to the user. The optional use of a memory element allows this information to be processed and/or provided or supplemented later. An interlinkage of sensor elements is also conceivable, for example, between a filling level sensor and a meter recording the time since the first opening of the liquid container.

The sensor data may also be transferred to an atomizer via an interface, which then performs evaluations or stores the data for further use. A corresponding interface is likewise comprised in a preferred embodiment of the liquid tank according to the present invention.

In a refinement of the present invention, the liquid tank provides a first mechanical coupling element, in particular, a bayonet element or a rotary bolt mechanism, in the surrounding region of the valve on a housing. In this way, the liquid tank can be easily and securely arranged on the atomizer and fastened in a way that ensures the reliability of the process. Preferably, a second mechanical coupling element, the geometry of which is formed correspondingly such that it can be connected to the first mechanical coupling element, is additionally comprised on a portion of the housing that is facing away from the valve. In this way, the liquid tanks can be coupled to one another. This serves, for example, for making storage easier or, if the coupling elements are of an appropriately stable form, may serve, for example, for extending the length of a handle. The liquid tank itself may also serve as the handle on the atomizer, or at least as part of the handle.

In the context of the present invention, an electrostatic atomization may also be understood as meaning an electro-hydrodynamic atomization.

In the context of the present invention, a liquid should be understood as meaning any kind of liquid. In the context of the present invention, it is provided, in particular, that the liquid is a cosmetic. The liquid may also be a liquid paint or lacquer or the like.

BRIEF DESCRIPTION OF THE DRAWINGS

An exemplary embodiment of the liquid container according to the present invention is schematically represented in the following figures.

DETAILED DESCRIPTION OF THE INVENTION

Figure 1:
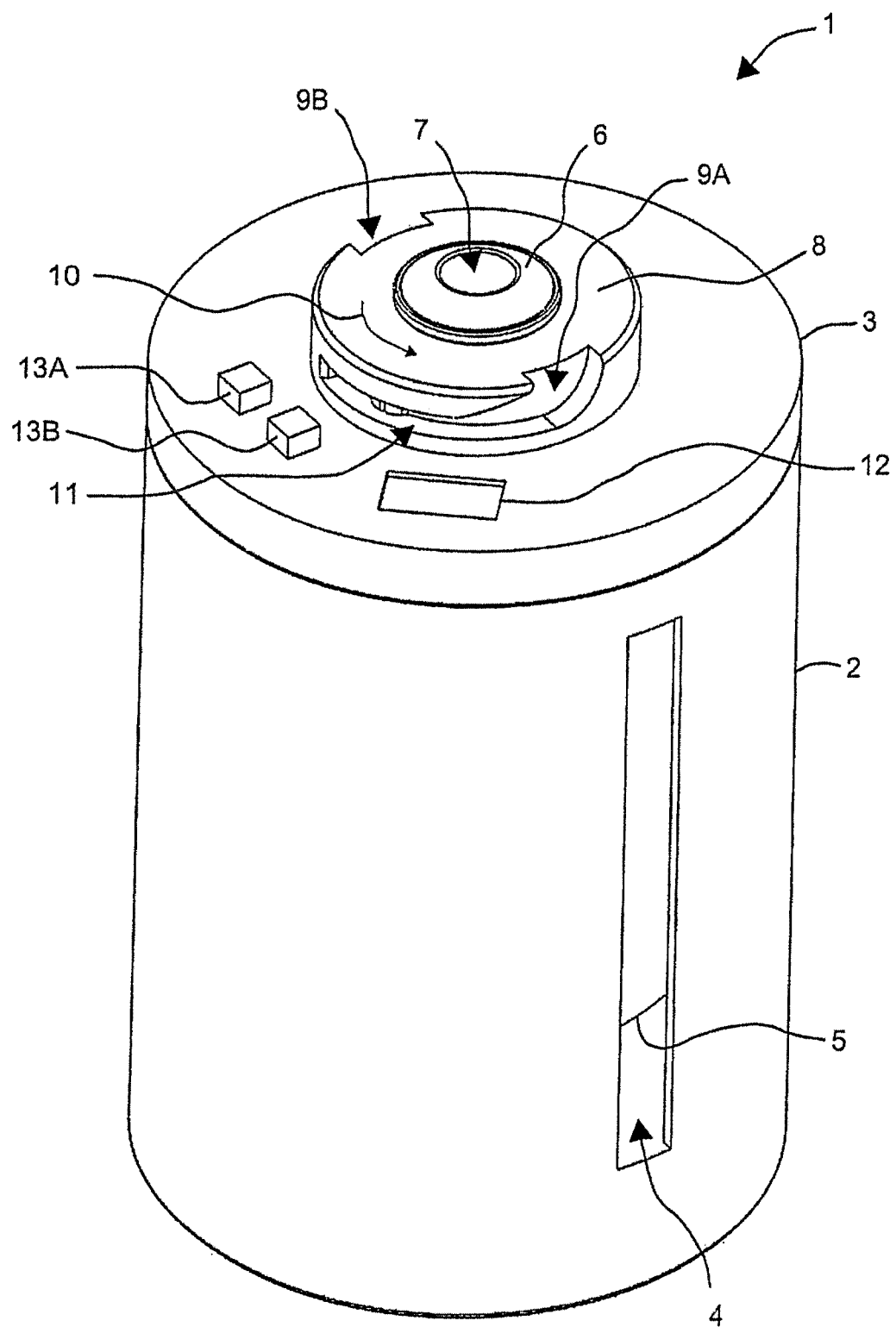
FIG. 1 shows a first liquid tank in a perspective representation, with a valve.

Specifically, FIG. 1 shows a first embodiment of a liquid tank 1. The liquid tank 1 in this case comprises a housing 2 and a housing cover 3. The housing 2 has on one side an opening 4, through which a bag 5 for receiving the liquid that is arranged in the housing 2 can be seen. The filling level of the bag 5 can be read off through the opening 4.

Arranged centrally on the housing cover 3 is a valve 6, in the present case in the form of a lip valve. The valve 6 has centrally an inlet opening 7 for an opening mechanism (not represented), which is provided on an atomizer and enters the inlet opening 7 when the liquid tank 1 is used.

Arranged surrounding the valve 6 is a coupling mechanism 8, the coupling mechanism 8 in the present case being formed as a rotary coupling. In this case, a projection arranged on the atomizer reaches into the grooves 9A, 9B and, by a turning movement in the direction 10 along the channel 11, is engaged in an interlocking manner. In this way, a simple, self-centering arrangement of the liquid tank 1 on an atomizer is ensured. The housing cover 3 also comprises devices for mechanical and/or electrical or electronic coding. Mechanical coding may be realized, for example, by a notch opening 12, in which a latch of the atomizer engages. An electrical coding may be achieved by the provision of a conductive bridge, for example, a conductive housing cover 3. For an electronic coding, information on a chip or other data carriers may be provided in one or more elements 13A, 13B. Wireless information, for example, an RFID, is also conceivable.

Figure 2:
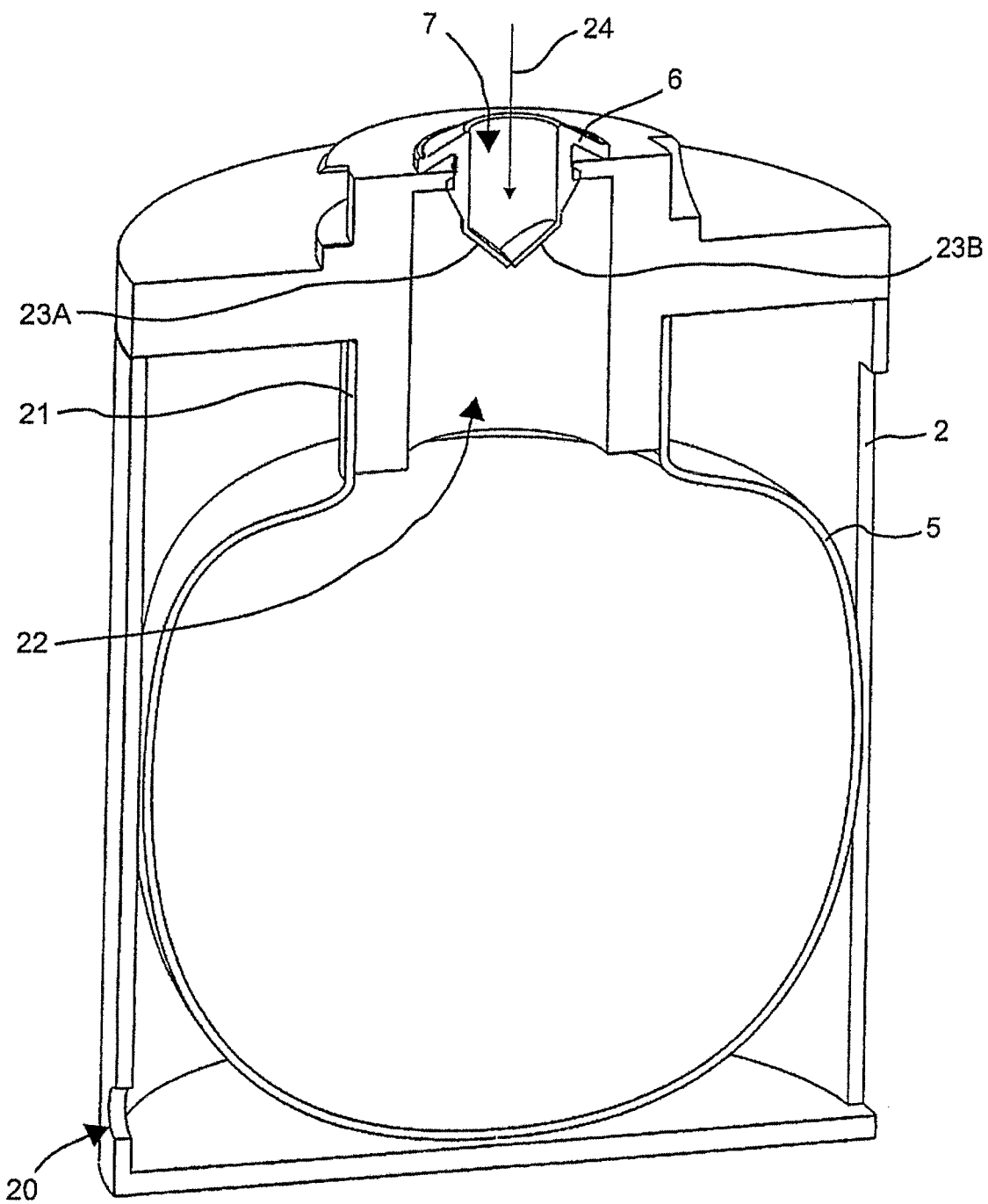
FIG. 2 shows a liquid tank in a sectional representation, with a valve and a flat bottom.

FIG. 2 shows a section through a liquid tank 1 corresponding to FIG. 1. The housing 3 has in this case an additional opening 20, which serves for aerating the interior space of the housing 2, in order that the released volume when the bag 5 collapses due to removal of the liquid cannot lead to a negative pressure in the interior of the housing.

The bag 5 is connected by way of a connection region 21 to an outlet channel 22 of the housing cover 3. This connection may be sealed either by elastic deformation or by way of clamping mechanism, in particular clips or rings.

At the upper end of the outlet channel 22, the lip valve 6 sits with the arranged valve lips 23A, 23B. If an opening mechanism is then inserted through the opening 7 in the direction 24, it penetrates the valve lips 23A, 23B and allows a removal of the liquid from the interior of the bag 5. If the opening mechanism is withdrawn, a flow of material from the interior of the bag 5 leads to a pressure on the valve lips 23A, 23B, whereby they are closed. For providing the corresponding material pressure, the bag 5 may have a certain elasticity or prestress, for example, in the form of a rubber balloon.

Figure 3:
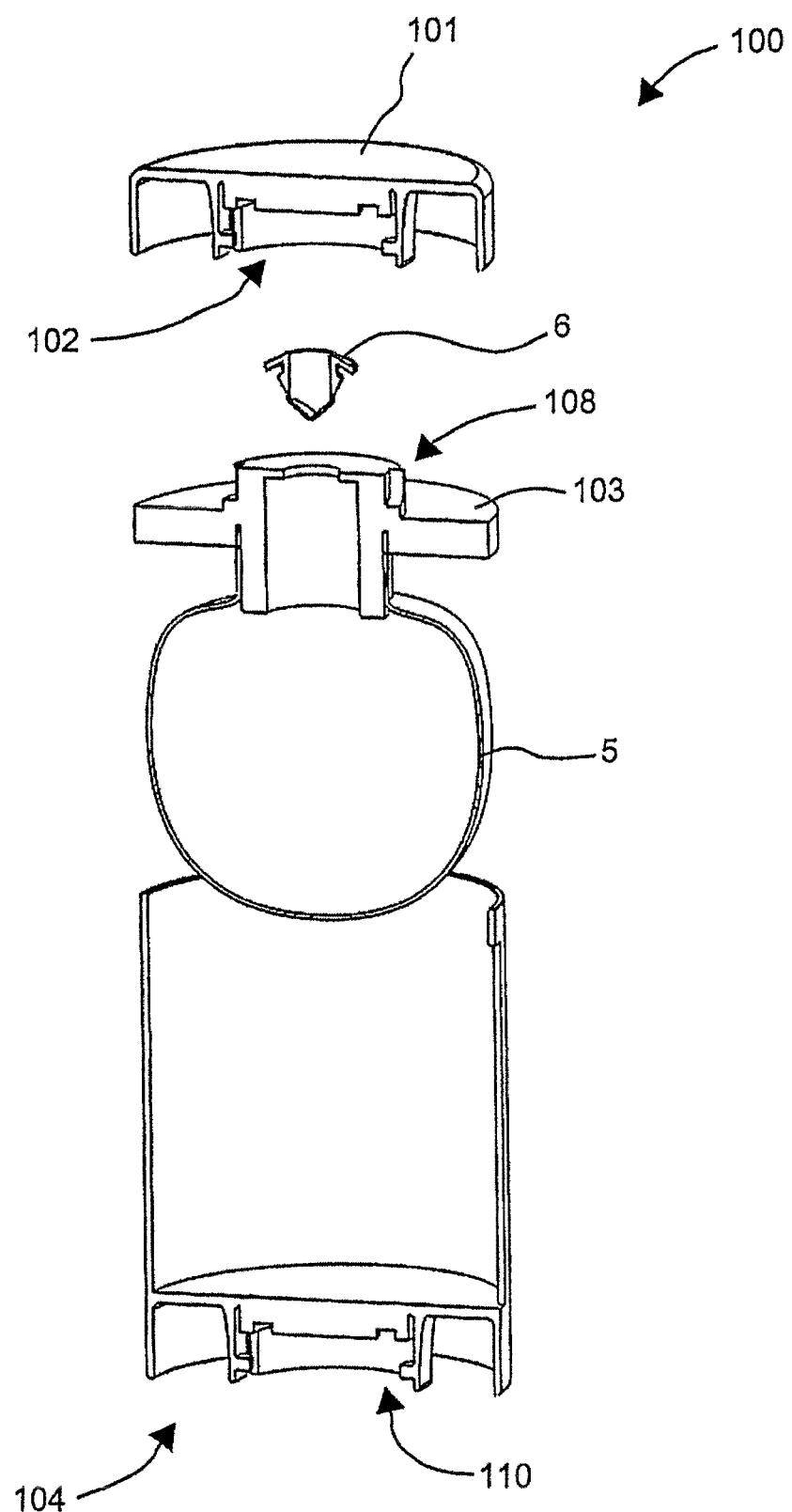
FIG. 3 shows a liquid tank in a sectional exploded representation, with a valve and a coupling element at the bottom.

FIG. 3 shows a further embodiment of a liquid tank 100 according to the present invention in an exploded representation. In comparison with the embodiment described above, the embodiment of the liquid tank 100 has an additional closure cover 101, which by way of corresponding coupling elements 102 can be introduced into the mechanical rotary coupling described above.

Furthermore, the liquid tank 101 has in the region of its bottom 104 a matching corresponding coupling element 110, which is chosen in its geometrical design in such a way that it can engage in a coupling element 108 of the housing cover 103 in the way described above. In this way, a number of liquid tanks 101 can be arranged one behind the other and can be fastened to one another. The further component parts of the liquid tank 101 correspond to the component parts described above and are denoted by the same designations.

Figure 4:
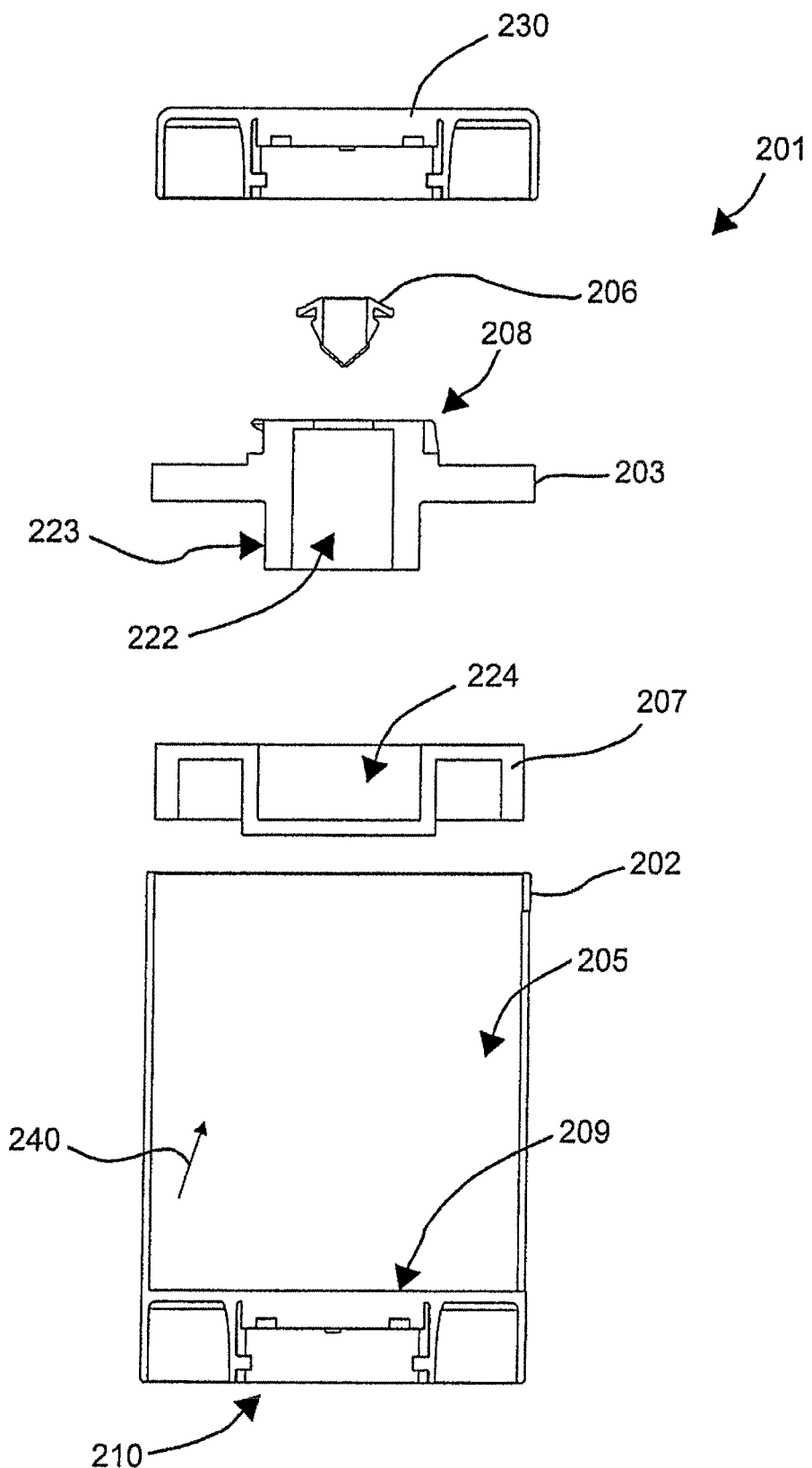
FIG. 4 shows a second liquid tank in a sectional exploded representation, with a valve and a coupling element and a passive follow-up piston.

FIG. 4 shows an alternative embodiment of a liquid tank 201 in an exploded representation. The liquid tank 201 in turn comprises a housing 202, a housing cover 203 and a lip valve 206. Instead of a bag for keeping the liquid, the interior space 205 of the housing 202 is now formed for receiving a liquid. When the liquid is removed through the lip valve 206, in that the liquid is, for example, sucked away by a suction pump, a passively entrained follow-up piston 207 follows the remaining volume of the liquid. Initially, when the liquid tank is completely filled, the follow-up piston 207 is arranged in the region of the lower housing bottom 209. As time passes, the piston moves in the direction 240 toward the outlet channel 222 of the housing cover 203. The lower projection 223 of the housing cover 203 may in this case enter a clearance 224 in the follow-up piston 207, in order as well as possible to allow complete emptying of the liquid tank 201.

In the region of the housing cover 203, the liquid tank 201 likewise comprises a coupling mechanism 208, which can correspondingly engage in the corresponding coupling mechanism 210 of another liquid tank 201, so that the liquid tanks 201 can likewise be arranged on one another. In addition, a closure cover 230 may also be provided in a way corresponding to the embodiment described above.

LIST OF DESIGNATIONS

1 Liquid tank
2 Housing
3 Housing cover
4 Opening
5 Bag
6 Valve
8 Coupling mechanism
9A, 9B Grooves
10 Direction of rotation
11 Channel
12 Notch opening
13A, 13B Coding element
20 Opening
21 Connection region
22 Outlet channel
23A, 23B Valve lips
100 Liquid tank
101 Closure cover
102 Coupling element
103 Housing cover
104 Bottom
110 Coupling element
108 Coupling element
201 Liquid tank
202 Housing
203 Housing cover
205 Interior space
206 Lip valve
207 Follow-up piston
208 Coupling mechanism
209 Housing bottom
210 Coupling mechanism
222 Outlet channel
223 Projection
224 Clearance
240 Direction of movement
230 Closure cover

The invention claimed is:

1. A liquid tank for an electrostatic atomizer for liquids, the liquid tank comprising:
 a housing;
 a housing cover;
 a receiving space for a liquid;
 a delimiting wall delimiting the receiving space with respect to a surrounding area within the housing; and
 a self-closing valve connecting the liquid tank to the electrostatic atomizer,
 wherein the delimiting wall is a flexible, collapsible bag,
 wherein the collapsible bag is connected to an outlet channel of the housing cover at a connection region via an elastic deformation connection, and
 wherein at least one of the delimiting wall and the housing consists of an insulating material defining an electrostatic shielding, and wherein the insulating material has a dielectric strength of at least 30 kV.

2. The liquid tank as claimed in claim 1, wherein the insulating material has a wall thickness of at least 1 mm.

3. The liquid tank as claimed in claim 1, wherein at least one of the delimiting wall and the housing comprises a contact for a reference potential with respect to a high voltage, and
   wherein the contact has at least one contact part connected to the electrostatic atomizer.

4. The liquid tank as claimed in claim 3, wherein the contact comprises a common negative pole or a common ground potential of a high-voltage source and a battery.

5. The liquid tank as claimed in claim 1, wherein the liquid tank further comprises a detector identifying the liquid tank,
   wherein the detector is provided as one of (1) a mechanical coding, for forming an interlocking engagement, (2) an electronic coding in the form of an RFID marking transmitting information about the liquid tank and receiving information about the liquid tank, and (3) an electrical coding forming electrical line routes via contacts.

6. The liquid tank as claimed in claim 1, wherein the liquid tank further comprises at least one further receiving space for a further liquid and a delimiting wall for delimiting the receiving space with respect to the surrounding area and the first receiving space.

7. The liquid tank as claimed in claim 1, wherein the liquid tank further comprises at least one filling level indicator indicating a filling level of the liquid in the receiving space.

8. The liquid tank as claimed in claim 1, wherein the liquid tank further comprises at least one sensor element detecting ambient parameters of the liquid tank and/or the liquid therein, and
   wherein the sensor element has a memory element storing the ambient parameters.

9. The liquid tank as claimed in claim 1, wherein the self-closing valve is one of a diaphragm, a lip valve, a ball valve, and a spring valve.

10. The liquid tank as claimed in claim 1, wherein the liquid tank further comprises a first mechanical coupling in a surrounding region of the self-closing valve on the housing, and a second mechanical coupling, the geometry of which corresponds to that of the first mechanical coupling so that the second mechanical coupling is adapted to be connected to the first mechanical coupling,
   wherein the second mechanical coupling is provided on a portion of the housing facing away from the self-closing valve.

11. The liquid tank as claimed in claim 10, wherein the first mechanical coupling comprises a bayonet or a rotary bolt mechanism.

\* \* \* \* \*